United States Patent [19]

Puckett

[11] 4,012,178

[45] Mar. 15, 1977

[54] HYDRAULIC PUMP WITH REPLACEABLE PUMPING MEMBER

[76] Inventor: Benjamin V. Puckett, 13529 Charlwood Circle, Cerritos, Calif. 90701

[22] Filed: Feb. 25, 1975

[21] Appl. No.: 552,927

Related U.S. Application Data

[62] Division of Ser. No. 351,461, April 16, 1973, Pat. No. 3,883,272.

[52] U.S. Cl. .................................. 417/478; 417/567
[51] Int. Cl.² ................... F04B 43/08; F04B 45/06
[58] Field of Search .......... 417/478, 479, 394, 567, 417/568; 285/347

[56] References Cited

UNITED STATES PATENTS

| 723,042 | 3/1903 | Schwern | 417/478 |
|---|---|---|---|
| 2,533,097 | 12/1950 | Dale | 285/347 |
| 3,262,446 | 7/1966 | Stoner | 417/478 |
| 3,282,223 | 10/1966 | Karkut | 417/478 X |
| 3,427,987 | 2/1969 | Eull | 417/478 X |
| 3,526,223 | 9/1970 | Curtis | 417/394 X |
| 3,551,076 | 12/1970 | Wilson | 417/385 |
| 3,620,653 | 11/1971 | Gaylord et al. | 417/568 |
| 3,814,547 | 6/1974 | Kitrilakis et al. | 417/478 |
| 3,822,966 | 7/1974 | McClocklin | 417/568 |

FOREIGN PATENTS OR APPLICATIONS

| 1,049,365 | 8/1953 | France | 417/383 |

*Primary Examiner*—Carlton R. Croyle
*Assistant Examiner*—Thomas I. Ross
*Attorney, Agent, or Firm*—George J. Netter; Patrick F. Bright; Elwood S. Kendrick

[57] ABSTRACT

A hydraulic pump particularly suited for the extracorporal circulation of blood, having a readily replaceable and disposable pumping member is disclosed. The pump avoids injury to the blood cells and creates a minimum of turbulence during the pumping operation, thus limiting the buildup of fibrin.

7 Claims, 6 Drawing Figures

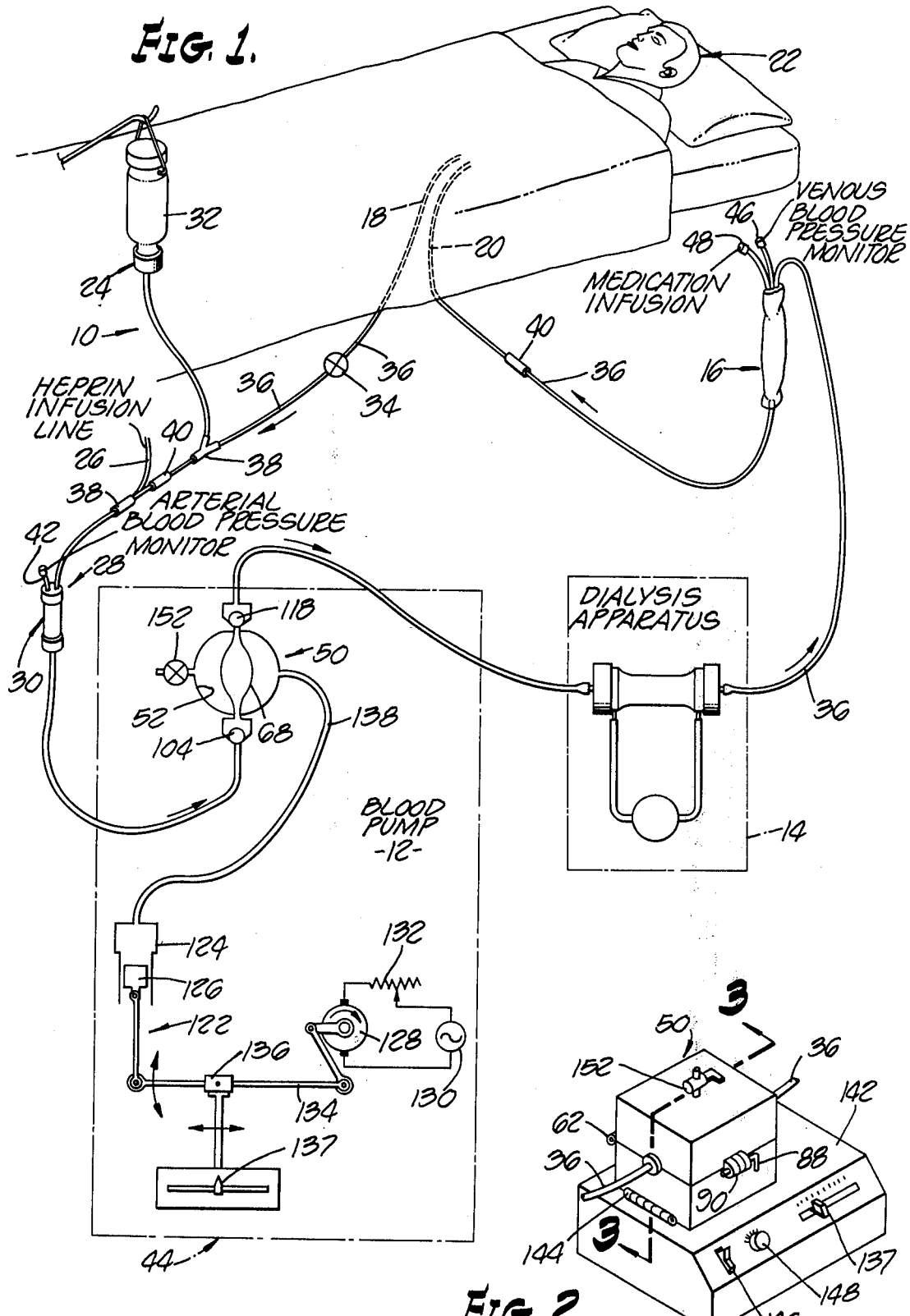

HYDRAULIC PUMP WITH REPLACEABLE PUMPING MEMBER

This is a division of application Ser. No. 351,461 filed Apr. 16, 1973, now U.S. Pat. No. 3,883,272.

In the past the most common method of extra-corporal circulation of blood involved the use of a tube pump in which circulating rollers would compress a circular section of tubing and force the blood through the system. The pressure on the blood cells from the mechanical deformation of the tubing, however, resulted in the destruction of the platelets of the blood cells, resulting in a high degree of haemolysis, which is injurious to the patient.

In recognition of the destruction to the blood, by the tube pump method, various forms of hydraulic pumps were employed for the circulation of blood. See, for example, U.S. Pat. Nos. 3,218,979, 2,832,294 and 3,099,260.

The previously available hydraulic blood pumps, however, were generally inadequate for multiple usages of short duration due to the general difficulty and cost of replacing those portions of the pump which had come into contact with the circulating blood. It is absolutely essential that after each occasion of pumping blood, all the component parts of the pump be in a sterile condition in order to prevent either the contamination of the previous user during a subsequent use, or to prevent the cross-contamination of different users of the same pump.

Rapid sterilization and replacement permits the cost per patient per use for such a pump to be held to a minimum.

A further disadvantage of the previously available blood pumps was the undersirable turbulence created within the pumping chamber. Such a turbulence greatly contributes to the creation of fibrin, which is a cause of coagulation of the blood. This turbulence is largely due to the location and operation of the inlet and outlet valves which regulate the flow of the blood within the pumping member.

An additional source of buildup of fibrin in the prior art devices is the turbulence resulting from wrinkles on the interior surface of the pumping member during its operation, such as shown in U.S. Pat. No. 3,218,979.

While pumping devices in the prior art had used a taut pumping member, such as disclosed in U.S. Pat. No. 2,812,716, such pumps are not readily replaceable and result in substantial fibrin buildup. The replacement of a taut pumping member has been particularly difficult for an untrained person in his home environment. Due to the growing home use of hemodialysis equipment (more generally known as the artificial kidney) it is essential that any such apparatus be easily and accurately used be the patient, who many times may be a young child.

OBJECTS

It is therefore an object of the present invention to provide a blood pumping apparatus which may be operated by one generally untrained in the operation of such pumps.

Another object of the present invention is to provide a blood pump which has inlet and exhaust valves that permit as laminar a flow of blood as possible to prevent the buildup of fibrin during the pumping operation of the pump.

An additional object of the present invention is to provide a blood pump in which the portions of the pump which come into contact with the blood during the pumping operation may be readily replaced.

Another object of the present invention is to provide a pumping member in which the portions of the pump which come into contact with the circulatory blood may rapidly be changed, with assurance that the parts have been properly aligned.

In the present invention, all of the portions of the improved blood pump which come into contact with the blood may be very readily replaced with a previously sterilized component, without fear of any contamination. Proper alignment devices insure the correct alignment of the replacement parts.

Inlet and outlet valves are inserted within an elastic tubular pumping member, controlling the flow of blood through the pumping member. The inlet and outlet valves are designed so as to minimize the turbulence created within the pumping member, thus limiting the buildup of fibrin within the circulating system.

Other objects, features, and advantages of the invention will become apparent from the following description of the improved blood pump and from the accompanying drawings.

In the drawings, which illustrate the best mode of the invention:

FIG. 1 is a perspective view of the pump used in cooperation with dialysis apparatus. Features of the pump are shown diagrammatically;

FIG. 2 is a perspective view of the pump with the pump in a loading position;

Figure 3:
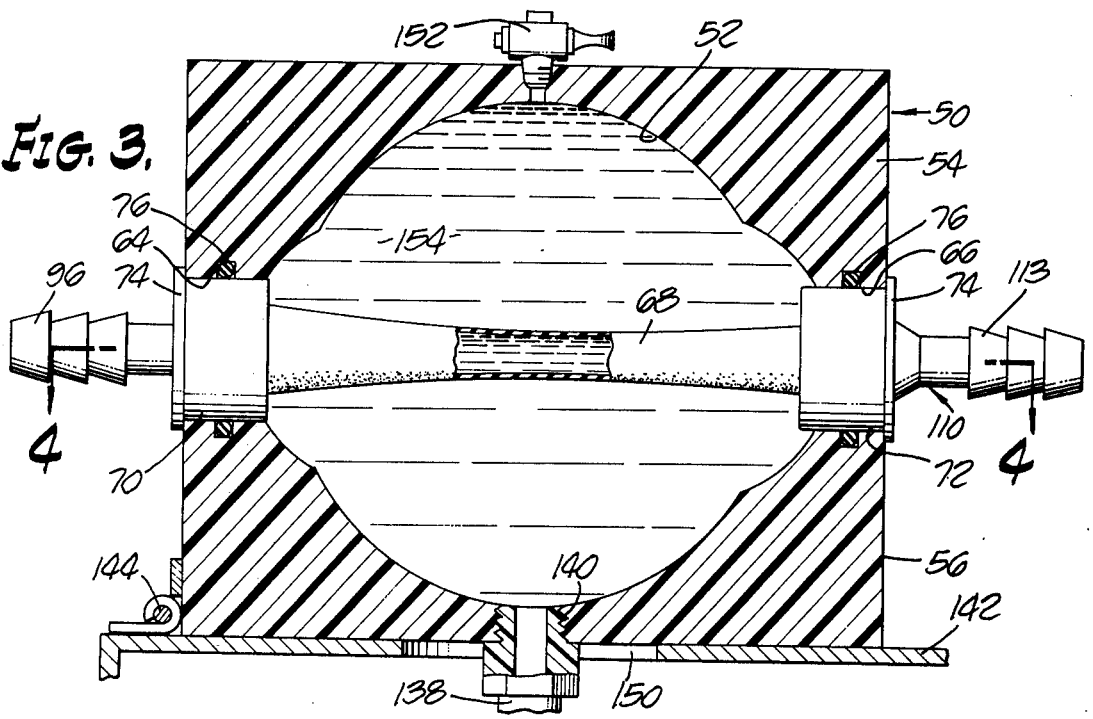
FIG. 3 is a sectional elevation view of the blood pump along lines 3—3 of FIG. 2.

It is to be understood that the improved blood pumping apparatus of the present invention is not limited merely to use in cooperation with hemodialysis equipment, as illustrated in FIG. 1, or even limited to medical applications only. Any system in which pure laminar flow is desirable for the prevention of the stagnation of the contents within the pumping apparatus, be it acidic or biological, may use the present apparatus to advantage. Also, any system requiring the pumping of a plurality of different materials, such as for pumping different chemicals may profitably employ the present invention. However, it is presently contemplated that the primary usage of the improved pumping apparatus will be in the medical field and in the preferred embodiment it is shown in use with hemodialysis equipment.

The illustration shown in FIG. 1 includes an arterial blood set 10, the improved blood pumping apparatus of the present invention 12, hemodialysis apparatus 14 and venous blood set 16. The arterial and venous connections 18 and 20 may be made to the patient 22 by either the conventional dual needle puncture or the more recently introduced single-needle puncture (not shown). The present improved blood-pumping apparatus will operate equally well with either of the two puncture systems.

The arterial blood set 10 comprise a saline infusion apparatus 24, for cleaning the system prior to use, a heparin infusion line 26 for introductory heparin, an anti-coagulant, into the system, and an arterial blood pressure monitor 28 having an arterial drip chamber 30. The saline infusion apparatus 24 includes a bottle of saline solution 32 and a valve 34 for preventing a back flow of the saline solution into the patient during the cleaning operation.

All of the tubing employed in the apparatus is of the type commonly used in the medical field which does not react with blood such as polyvinyl chloride or similar plastic materials. When the device is used in fields other than medicine, appropriate tubing is used, depending on the particular application of the pump.

The saline infusion apparatus 24, the heparin infusion line 26, the arterial blood pressure monitor and drip chamber 28 and 30 are introduced into the connecting tubing 36 by means of appropriate Y joints 38 placed in the system. Also distributed throughout the system are self-sealing tap joints 40, for permitting the sampling of the contents of the tubing should it be so desired. The arterial drip chamber 30 dissipates any air bubbles which might be present in the system. Access to the drip chamber is provided through a suitable access stub 42.

The blood flows from the arterial blood pressure monitor 28 through tubing 36 to blood pump 12, having suitable controls 44 for varying the frequency and quantity of fluid flow. From the blood pump the fluid passes through the hemodialysis apparatus 14, through the venous blood pressure indicator 16, having medication infusion inlets 46 and 48, and finally through tubing 36 back to the patient 22.

The blood pump 12 of the present invention comprises a blood pump head 50, resting on a casing 142. The controls 44 for the blood pump are enclosed within casing 142.

Figure 4:
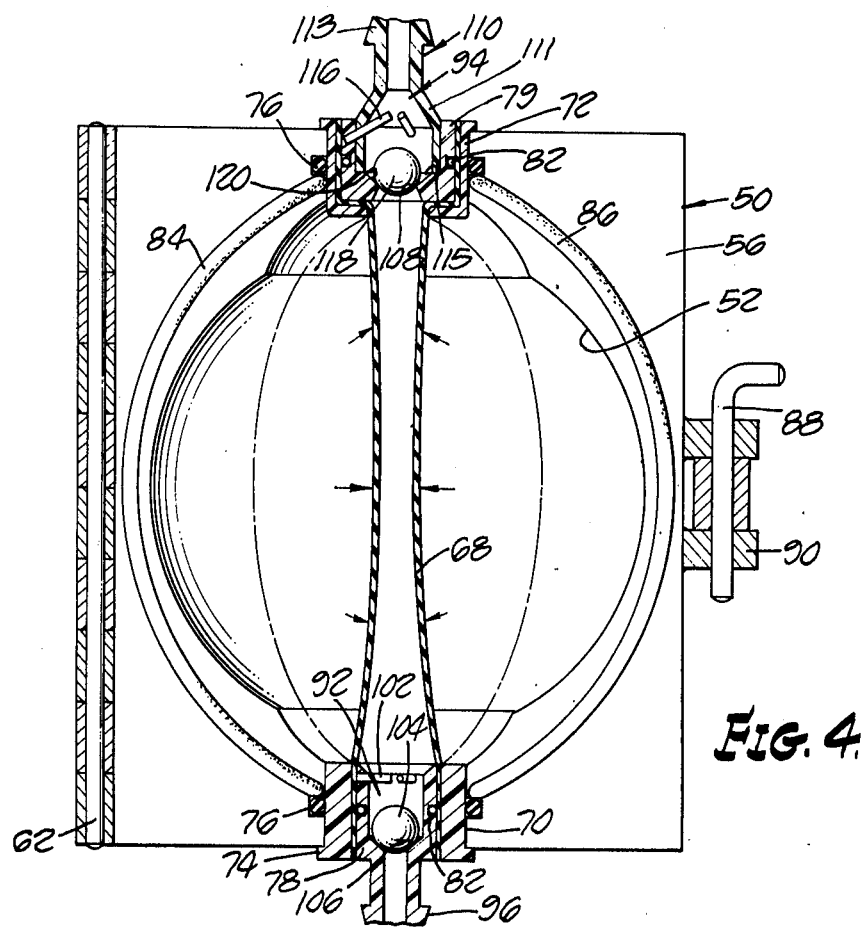
FIG. 4 is a sectional plan view of the blood pump along lines 4—4 of FIG. 3.

The blood pump head 50 is better shown in FIGS. 3 and 4. The blood pump head is transparent, made of a sturdy plastic or glass, and includes a chamber 52 formed of two casing halves 54 and 56, having semispherical cavities therein, and connected to one another, and rotatable around, hinge 62.

The blood pump head 50 has apertures 64 and 66, formed by semicircular cut outs on the side walls of casings 54 and 56, in which a tubular pumping member 68 of elastic non-reactive material, such as rubber, is supported at its ends in fluid sealing engagement, by sealing rings 70 and 72.

Each sealing ring 70 and 72 has an outwardly extending lip having an outer diameter slightly larger than the inner diameter of apertures 64 and 66. It is not necessary that the lip 74 extend entirely around the periphery of the sealing ring 70 since this lip is not utilized for fluid sealing purposes but is primarily an alignment and holding device.

The manner in which the tubular pumping member 68 is retained in fluid sealing engagement with the walls of the pump head 50 may be more clearly seen in FIG. 4. Sealing rings 70 and 72 have around their periphery an O-ring 76. The O-ring forms a fluid sealing barrier when the sealing ring 70 is placed within apertures 64 and 66.

Within each end of the tubular pumping member 68 is an inner sealing ring 78 and 79, the inner rings 78 and 79 having an outer diameter slightly smaller than the inner diameter of the outer sealing rings 70 and 72. An annular circumferential groove 80 is present on the outer surface of each inner sealing ring for receiving a second O-ring 82.

The tubular pumping member 68 has its ends inserted within sealing ring 70 and 72 and within the opening of the tubular pumping member is placed the inner sealing rings 78 and 79. Outwardly extending O-ring 82 is forced in contact with the inner circumference of the tubular pumping member 68, thereby forming a fluid sealing juncture between the outer sealing rings 70 and 72 and the inner sealing rings 78 and 79.

Casings 54 and 56 are maintained in fluid sealing arrangement with one another by rubber sealing mounts 84 and 86. Locking pin 88 cooperates with extending flanges 90 to lock casings 54 and 56 together to prevent their accidental separation.

An inlet valve 92 is located within inner sealing ring 78 while an outlet valve 94 is located within inner sealing ring 79. The inlet valve is better shown in FIG. 5.

Figure 5:
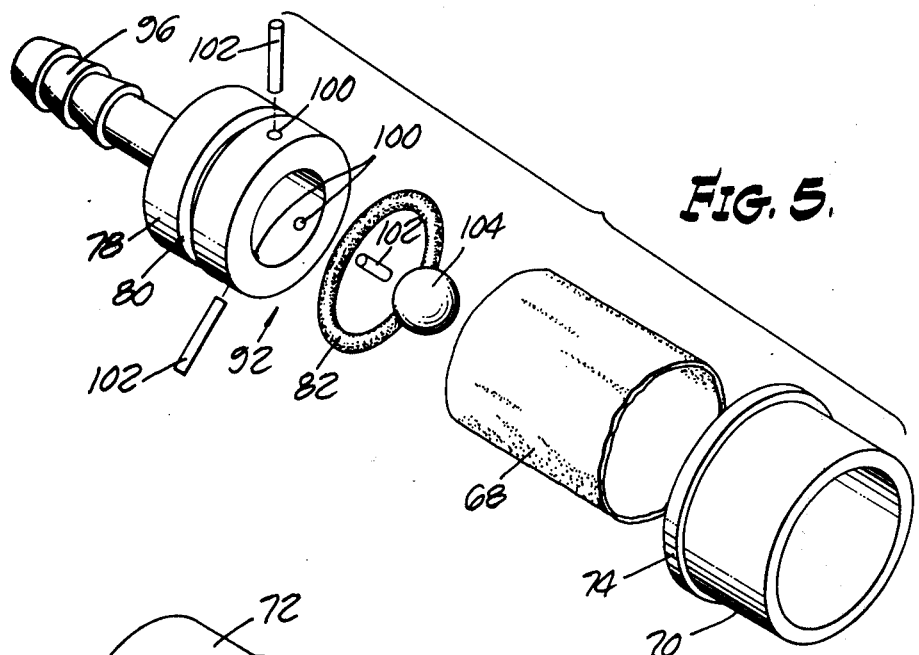
FIG. 5 is an exploded perspective view of the inlet valve of the pumping member of FIG. 4.

FIG. 5 is an exploded perspective view of the inlet valve 92. The inner sealing ring 78 has a connecting extension 96 integral therewith having a narrowed passageway permitting access to the larger interior of the sealing ring 78.

At the end of the inner sealing ring 78 distant from the connecting extension 96, there are located three symmetrically placed holes 100 through the wall of the inner sealing ring 78. While the symmetrical placement of the holes 100 is the preferred form of the invention, this is not essential to the operation of the improved blood pump. Similarly, although the holes are illustrated as being perpendicular to the longitudinal access of the inner sealing ring 78 this may be varied.

Placed within each of the holes 100 in the inner sealing ring 78 are short dowel-like projections or pins 102, one end of each pin terminating within the opening of the inner sealing ring 78 and the second end of each pin 102 terminating within the wall of the inner sealing ring 78.

Within the large opening of the inner sealing ring 78 is located a small stainless steel ball 104. The ball 104 is restrained from travel in one direction by the projecting pins 102 and restrained in the other direction by the smaller inner diameter of the connecting extension 96. The edges of the narrowed passage of connecting extension 96 are beveled 106 to permit the ball 104 to sealably seat itself within the passageway, thus blocking fluid flow.

Within the other inner sealing ring 80 is located an outlet valve 94. The outlet valve may be better seen from FIG. 6.

Figure 6:
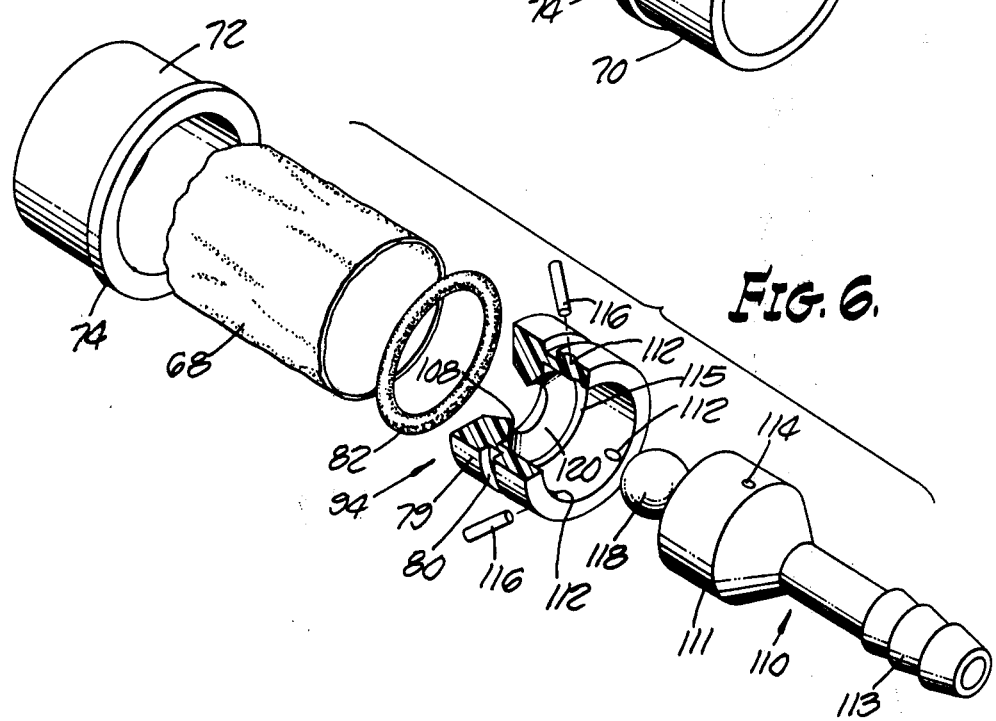
FIG. 6 is an exploded perspective view of the outlet valve of the pumping member of FIG. 4.

FIG. 6 is an exploded perspective view of the outlet valve 94. The opening at the inner end of inner sealing ring 79 has a portion with a smaller inner diameter 108 than the distant end of the inner sealing ring. Connecting extension 110, having a hollow conical base portion 111 and a tubular extension piece 113, having a reduced inner diameter from that of the conical base 111, fits within the large inner diameter portion of the inner sealing ring 79, seating itself on shoulder 115. Inner sealing ring 79, illustrated in FIG. 6, has three symmetrically placed holes 112 through the wall of the inner sealing ring 79. In alignment with the holes 112 of the inner sealing ring 79 are located three holes 114 in the conical base 111 of the connecting extension 110. (Only one of the three holes being visible in FIG. 6). The angle of holes 112 and 114 are illustrated as forming an acute angle with the longitudinal access of the inner sealing ring 79.

Pins 116 are inserted through holes 112 and 114 with one end of the pins terminating with the opening of connecting extension 110 and the other end of the pin terminating within the wall of inner sealing ring 79. Due to the bias of the holes 112 and 114 in the sealing ring and the connecting extension, the pins slant outwardly from the tubular pumping member.

Located within the larger diameter portion of the conical base connecting extension 110 is located a second stainless steel ball 118, which is restrained from movement in the outer direction by pins 116 and from travel in the inner direction by the narrowing diameter 108 of the inner sealing ring 79. The narrow inner diameter portion of sealing ring 79 has its edges beveled 120 to permit the ball 118 to seat itself within the reduced opening and thus preventing flow of fluid through the valve 94.

Fluid chamber 52 of the pumphead 50 is joined to a pump 122 having a pumping chamber 124 and a piston 126 in fluid sealing engagement with the walls of the pumping chamber 124. The pump is operated by a variable speed motor 128 operated by an AC power supply 130. The speed of the motor 128 may be varied by adjustable rheostat 132. Reciprocal motion is imparted to piston 126 by a lever arm configuration 134 pivoted at a fulcrum 136. By varying the lateral position of the fulcrum 136, by means of slide knob 137, the stroke of piston 126 may be varied.

The fluid chamber 52 of the blood pumphead is joined to the pump chamber 124 by means of appropriate tubing 138 which passes through an aperture 150 in the housing 142. Bushing 140, having threads on its outer diameter, locks bushing 140 to the lower casing 56.

The pumphead 50 rests on housing 142 and is rotatably mounted to the housing by hinge 144 permitting rotational movement of the pumphead 50. The pump 122 and the motor 128 are enclosed within the housing 142 with the appropriate controls, such as on-off switch 146, motor speed control 148 and stroke control 137, accessible from the outside of the housing 142.

The hinge 144 is located in such a position on the top surface of casing 142 that, when blood pumphead 50 is rotated 90°, inlet connecting extension 96 does not hit the casing. The tubing 138 is of such a length that the blood pumphead 50 may be rotated through 90° without straining the tubing 138.

During the operation of the pump, the blood pumphead 50 is positioned, as shown in FIG. 2, with the tubular pumping member 68 in a horizontal position. Casings 54 and 56 are locked together in fluid sealing engagement. Fluid 154, which is initially stored in the pumping chamber 124 and in the tubing 138 is forced into pumphead chamber 52 as piston 126 rises within the pumping chamber 124. As the piston 126 approaches the top of its stroke, there is sufficient fluid within the system so that virtually the entire chamber 52 is full of fluid. The air within the pumphead chamber 52 is forced through air valve 152, leaving substantially no air within the pumphead chamber 52. Air valve 152 is closed to prevent the inflow of air back into the chamber 52.

After the air valve 152 is closed, the blood pumphead 50 is rotated 90° around hinge 144 so that the tubular pumping member 68 is in a vertical position. While in such a position, steel ball 104 within inlet valve 92 is held by gravity within the beveled portion 106 of the inlet valve 78 and thus blocks access of fluid to the tubular pumping member. At the same time, steel ball 118 is seated within the beveled portion 115 of the reduced diameter opening of inner sealing ring 79 of the outlet valve 94.

As the piston 126 begins its downward stroke, the fluid which is within pumphead chamber 52 is withdrawn, creating a partial vacuum within pumphead chamber 52. The partial vacuum causes the expansion of elastic tubular pumping member 68, creating within the tubular pumping member 68 a partial vacuum. Fluid is drawn through inlet valve 92 by the partial vacuum which also lifts ball 104 out of its seat 106. The ball 104 is restrained by pins 102 from entering the tubular pumping valve 68.

While the fluid is being drawn through the inlet valve 92 the partial vacuum within the tubular pumping member 68 acts upon stainless steel ball 118 within the outlet valve 94 to hold the ball 118 in its seat 115 closing the outlet valve and preventing fluid from passing through the outlet valve.

As the piston 126 continues its downstroke, the tubular pumping member 68 continues to expand until the piston reaches its bottommost point. As the piston again begins to rise within the pump chamber 124, the fluid is forced back into fluid chamber 52, placing pressure on tubular pumping member 68. The resultant increased pressure within the tubular pumping member 68 serves to force ball 104 of the inlet valve back into its seat 106 closing the inlet valve. In the outlet valve 94 the ball 118 is forced upwards out of its seat 115, permitting the blood within the tubular pumping member 68 to be pumped through the outlet valve. Ball 118 is restrained from blocking the narrow passageway of outlet connecting extension 113 by pins 116. The blood flows through the tubes 36, the dialysis apparatus 14, the venous blood pressure set 16, and then back to the patient 22. The pumping cycle continues as piston 126 continues to rise and fall within the pumping chamber 124.

When the use of the pump is no longer required or it is to be used for a new patient, blood pumphead 50 is rotated from the vertical position around hinge 144 back to the horizontal position resting upon the top surface of housing 142. The air valve 152 is opened permitting air to enter the pumphead chamber 52. Piston 126 is brought to its lowest point (if it is not already there) by setting rheostat 148 to operate the pump at its lowest speed, and observing whether all of the fluid has been evacuated from the transparent blood pumphead 50.

When all of the fluid 154 has been withdrawn pin 88 is withdrawn from flange 90 permitting upper casing 54 to be pivoted around hinge 62 revealing the tubular pumping number 68. The portions of the improved blood pump which had come into contact with the blood during the prior operation of the device would now be removed. Thus, sealing rings 70 and 74, inlet valve 92, and tubular pumping member 68, sealing rings 72 and 79, outlet valve 94, as well as O-ring 76, would be lifted out of the apertures 64 and 66 in the blood pumphead 50. All of the removed apparatus could then either be discarded or sterilized for further use. It is contemplated, however, that the economics involved in manufacturing the removed items would dictate that it would be more convenient and safer to discard these parts rather than re-use them.

A new unit consisting of all of the previously removed parts would then be easily placed into the pumphead 50. Alignment lips 74 would insure that the proper positioning of the sealing rings 70 and 72 took place. The lips 74 would also ensure that the proper tension was placed upon tubular pumping member 68 so that no wrinkles appear in the tubular pumping member which might cause the development of fibron during the pumping operation of the device.

It is also contemplated that O-ring 76 would be discarded, although these O-rings were not in contact with the blood during the pumping stage. However, by disposing of the O-rings 76, the replacement of the parts may be more quickly performed.

Once the tubular pumping member 68 has been fixed in place, upper casing 54 is rotated around hinge 62 until it rests upon casing 56. Sealing mounts 84 and 86 assure that casings 54 and 56 will be in fluid sealing engagement. Locking pin 88 is once again inserted within the flange 90, thus preventing accidental opening of the blood pumphead 50.

Piston 126, which had been in its lowest position during the replacement operation is now advanced into pumping chamber 124 thus driving fluid into the chamber 52. When the fluid has filled the chamber, thus driving all of the air within the chamber through the air valve 152, the air valve is again closed to prevent the entrance of air back into the chamber. The blood pumphead is then rotated 90° around hinge 144 until the tubular pumping member 68 is in a vertical position. The pump is once again ready for operation.

It should be noted that a minimum of turbulence is created within the inlet valve 92, the outlet valve 94 or the tubular pumping member 68. This is in part due to the beveling of all areas in which blood will flow, thereby substantially reducing the possibility or turbulence by having smooth flow surfaces. This is in greater part, however, due to the novel configuration of the inlet and outlet valves 92 and 94, in which pins 102 and 116 limit the movement of the steel balls 104 and 118 of the inlet and outlet valves with a minimum of interference in the laminar flow of the fluid.

In all of the prior art devices, the valves used have resulted in areas within the pumping chambers which have substantial dead flow spots or severe turbulence. This is atypical to the requirement that there be no areas within a blood flow path in which the buildup of fibron can occur.

Also, by having the tubular pumping member 68 taut during the pumping stage and further expanded during the intake stage, the possibility of wrinkles occurring within the tubular pumping member 68 is reduced. This avoids the interference in the laminar flow of the fluid which results when cylindrical pumping bulbs, such as disclosed in U.S. Pat. No. 3,218,979, are used.

Further means of preventing the buildup of fibron is having the tubular pumping member oriented in a vertical direction during the pumping operation. In such a manner, the force of gravity acts upon the blood, drawing the blood downward into the inlet valve, whenever a contrary force is not exerted upon the blood. This prevents or at least reduces the possibility that stagnant blood will merely rest on the surface of a horizontally aligned pumping member. The present invention thus further reduces the possibility of the buildup of fibrin.

While the preferred embodiment of the improved blood pumping apparatus has been disclosed, it will be evident to those skilled in the art that modifications may be made to the described device without departing from the spirit and the scope of the concept disclosed in the above description.

What is claimed is:

1. A hydraulic pump comprising a casing and a pumping unit comprising:
    a. a fluid impermeable elastic tubular member;
    b. a first and second pair of sealing rings sealingly connected to said elastic tubular member, each pair having:
        1. an outer tubular ring surrounding a portion of the outer wall of said elastic tubular member, said outer tubular ring including means for aligning and holding said sealing rings in said casing;
        2. an inner tubular ring within said elastic tubular member and having an annular groove around the outer circumference of said inner tubular ring;
        3. an O-ring within said annular grooves of said first and second inner tubular rings, said O-rings being in fluid sealing engagement with the inner surface of said elastic tubular member;
    c. said first pair of sealing rings having an inlet valve within the inner tubular ring, and
    d. said second pair of sealing rings having an outlet valve within the inner tubular ring, said elastic tubular member and said first and second pair of sealing rings defining a disposable unit which may be inserted in, or removed from the interior chamber of said casing which comprises means for creating alternately positive and negative pressure within the chamber to intermittently expand said elastic tubular member in said interior chamber.

2. The apparatus of claim 1 in which said inlet valve comprises:
    a. said inner tubular ring having a section of reduced inner diameter
    b. at least one projection extending radially inwardly into the interior of said inner tubular ring at a point proximate the interior of said elastic tubular member,
    c. a ball located within said inner tubular ring, said ball having a diameter larger than the reduced inner diameter portion of said inner tubular ring, said ball restrained by said projections from entering said elastic tubular member.

3. The apparatus of claim 1 in which said outlet valve comprises:
    a. said inner tubulor ring having a section of reduced inner diameter proximate the interior of said elastic tubular member,
    b. a connecting extension tubular member having a first section with an outer diameter slightly smaller than the large inner diameter of the inner tubular ring, said section fited within the inner tubular ring, and a second portion of said connecting extension tubular member having an inner diameter smaller than the inner diameter of the portion of the connecting extension tubular member inserted within the inner tubular ring,
    c. at least one projection extending radially into the interior of the connecting entension tubular member at a point away from said elastic tubular member,
    d. a ball located within said connecting extension tubular member having a diameter larger than said reduced diameter section of the inner ring and restrained by said projections from entering the reduced inner diameter of the connecting extension tubular member.

4. The apparatus of claim 3 in which said at least one projection extending radially into the interior of the inlet and outlet valves comprises at least three pins.

5. The apparatus of claim 3 in which said at least one projection extending radially into the interior of the inlet and outlet valves comprises at least three pins.

6. The apparatus of claim 5 in which said pins are symmetrically spaced from one another.

7. The apparatus of claim 1 in which said means for aligning and holding said sealing rings in said casing is a skirt on the outer tubular ring of each sealing ring, said skirt projecting radially outward from said outer tubular ring.

* * * * *